(12) United States Patent
Tice

(10) Patent No.: US 7,846,320 B2
(45) Date of Patent: Dec. 7, 2010

(54) SELF-ADJUSTING ELECTROCHEMICAL SENSOR

(75) Inventor: Lee D. Tice, Bartlett, IL (US)

(73) Assignee: Honeywell International Inc., Morristown, NJ (US)

( * ) Notice: Subject to any disclaimer, the term of this patent is extended or adjusted under 35 U.S.C. 154(b) by 732 days.

(21) Appl. No.: 11/868,318

(22) Filed: Oct. 5, 2007

(65) Prior Publication Data

US 2008/0024315 A1    Jan. 31, 2008

Related U.S. Application Data

(62) Division of application No. 10/925,750, filed on Aug. 25, 2004, now Pat. No. 7,297,242.

(51) Int. Cl.
*G01N 27/403* (2006.01)

(52) U.S. Cl. .................. 205/775; 204/401; 204/406; 204/431; 73/1.06

(58) Field of Classification Search .............. 204/401, 204/406, 400, 431; 205/775, 782, 787; 73/1.06
See application file for complete search history.

(56) References Cited

U.S. PATENT DOCUMENTS

| 5,328,847 A | 7/1994 | Case et al. |
| 5,999,121 A * | 12/1999 | Salonen ................ 342/351 |
| 6,049,283 A | 4/2000 | Lindsay |
| 6,428,684 B1 | 8/2002 | Warburton |

FOREIGN PATENT DOCUMENTS

WO      WO 00/14523 A2      3/2000

* cited by examiner

*Primary Examiner*—Kaj K Olsen
(74) *Attorney, Agent, or Firm*—Husch Blackwell LLP Welsh Katz

(57) ABSTRACT

A gas detector with a compensated electrochemical sensor exhibits altered sensitivity in response to decreasing stochastic noise in an output thereof. A gain parameter can be adjusted to alter sensitivity. A life-time estimate can be made based on sensitivity.

24 Claims, 4 Drawing Sheets

052604COtestN2
GAS RESPONSE TEST

052604COtestN2
GAS RESPONSE TEST

— Vblu

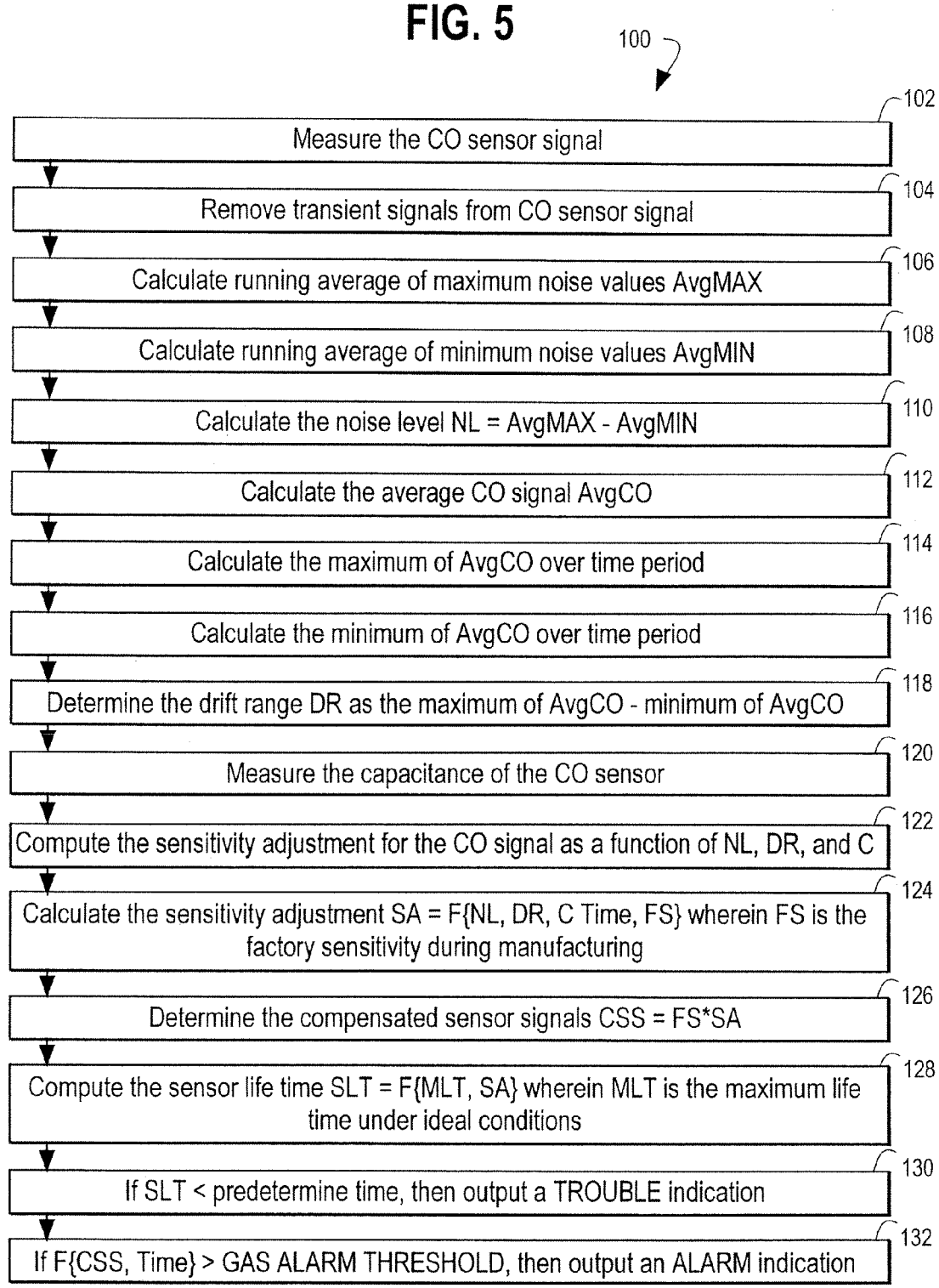

SELF-ADJUSTING ELECTROCHEMICAL SENSOR

CROSS-REFERENCE TO RELATED APPLICATION

This application is a Division of and claims the benefit of the filing date of U.S. patent application Ser. No. 10/925,750 filed Aug. 25, 2004 now U.S. Pat. No. 7,297,242 and entitled "Self-Adjusting Electrochemical Sensor".

FIELD OF THE INVENTION

The invention pertains to gas detectors. More particularly, the invention pertains to gas detectors having age-compensated electro-chemical sensors.

BACKGROUND OF THE INVENTION

Depending on the circumstances it can be desirable and/or particularly important to be able to sense the presence of various gases which might be dangerous or explosive. These include carbon monoxide, carbon dioxide, propane, methane, as well as other potentially explosive gases.

A variety of sensors are known which can detect various gases. These sensors are based on different technologies and have different performance characteristics and different cost characteristics. One technology of ongoing interest is represented by electrochemical sensors. This class of sensors is potentially reliable and inexpensive.

Electrochemical sensors can be designed so as to be responsive to a gas of interest and to be highly sensitive. They respond to a gas of interest with a respective output current. However, such sensors have a zero output current failure mode and zero output current in the absence of the selected gas. Because there is no specific failure indicator, external circuits have to be designed to supervise these types of sensors.

It has been known to use electrical stimulus to apply a current to such sensors, to measure the sensor's signal over time, and calculate a capacitance value. This capacitance value can indicate that the sensor(s) has (have) degraded beyond a predetermined threshold, or, it can be an indication the sensor has been removed from the circuit. However, by itself, it does not indicate the sensitivity of the respective electrochemical sensor.

Another prior art method measures an electrical noise in a sensor output signal. A trouble condition or indication can be output if the noise level falls below a predetermined fixed threshold. This method is based in a known characteristic; that as gas concentration increases, the sensor(s) not only output a signal indicative thereof, they also exhibit increased noise. FIG. 1A is a graph of output noise vs. gas concentration in parts per million which illustrates this characteristic. FIG. 1B illustrates exemplary response of an electrochemical sensor to a pulse of 100 ppm of CO. FIG. 1C illustrates increasing noise in response to exposure to the CO. However, this method does not teach maintaining the sensitivity. It only provides an indication of a failed sensor relative to a fixed threshold.

BRIEF DESCRIPTION OF THE DRAWINGS

FIG. 5 is a flow diagram of another aspect of the present invention.

DETAILED DESCRIPTION OF THE EMBODIMENTS

Figure 1A:
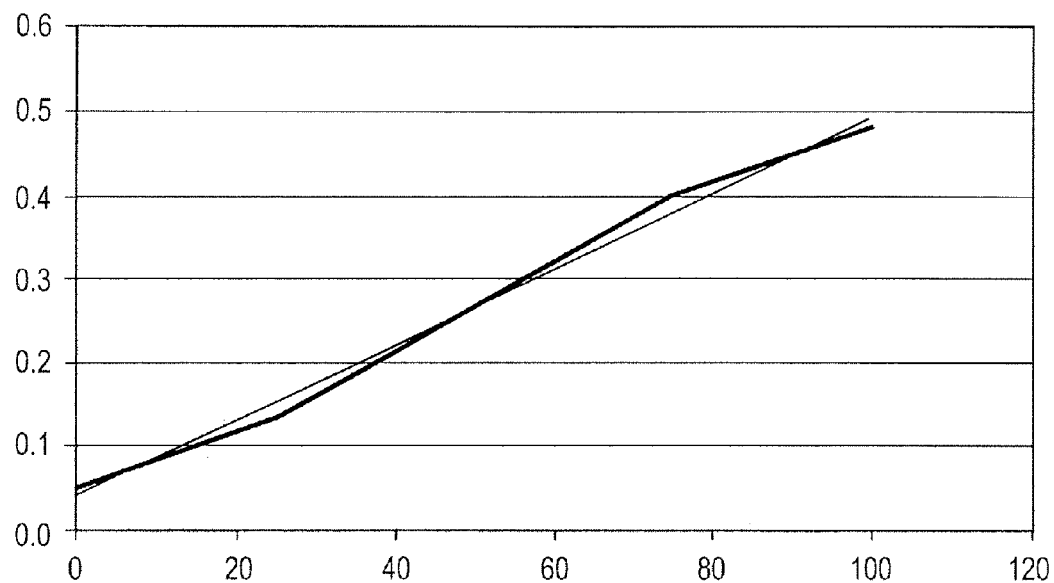
FIG. 1A is a graph illustrating variations in sensor noise as a function of parts per million of a selected gas.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

A disclosed embodiment of the invention overcomes the problems with monitoring the sensitivity of an electrochemical sensor over time. There are at least four active components that can be used to determine the condition of the sensor. These include the noise level in the sensor's output signal, the drift in the signal over time, the internal capacitance of the sensor, and the internal impedance of the sensor.

The sensor noise level will increase as the signal increases relatively proportionate to ambient gas concentration. When the sensor is detecting ambient gas, the increase in noise can be correlated against the signal increase from the electrochemical gas sensor. A function that combines the noise level in the absence of gas and the noise level with gas can be used to calculate a sensitivity adjustment factor that is applied to the gas signal to determine the local levels of ambient gas.

The electrical noise in the sensor can be combined with other electrical signals from the electrochemical sensor to determine the sensitivity thereof. A prediction can be made as to remaining lifetime of the sensor.

Figure 1B:
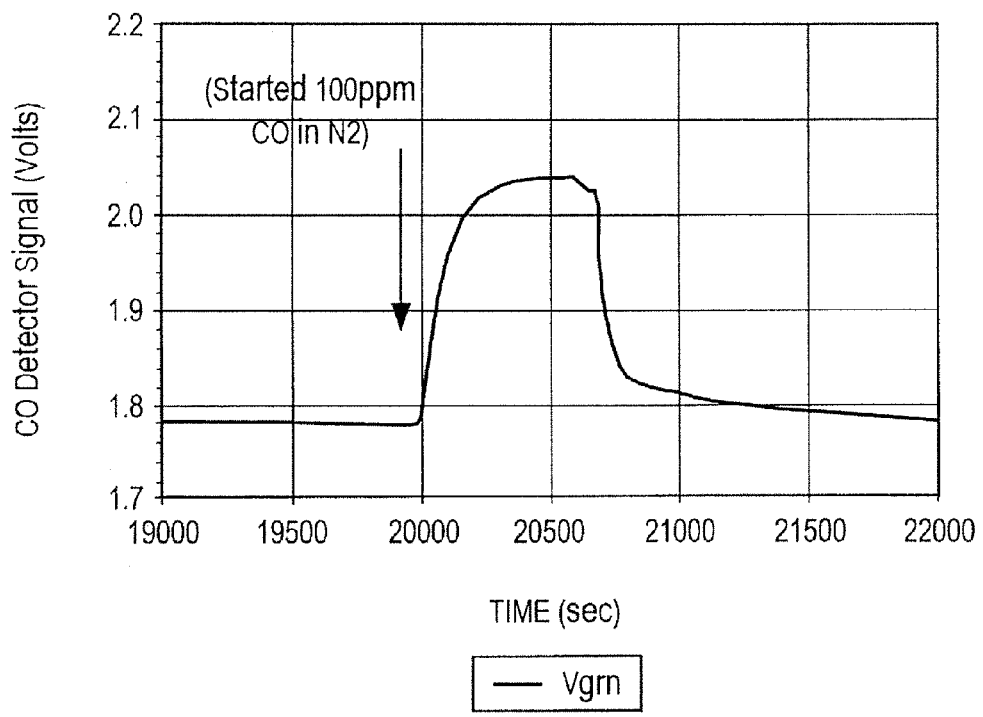
FIG. 1B is a graph illustrating increase of sensor output signal in response to the presence of a selected gas.
Figure 1C:
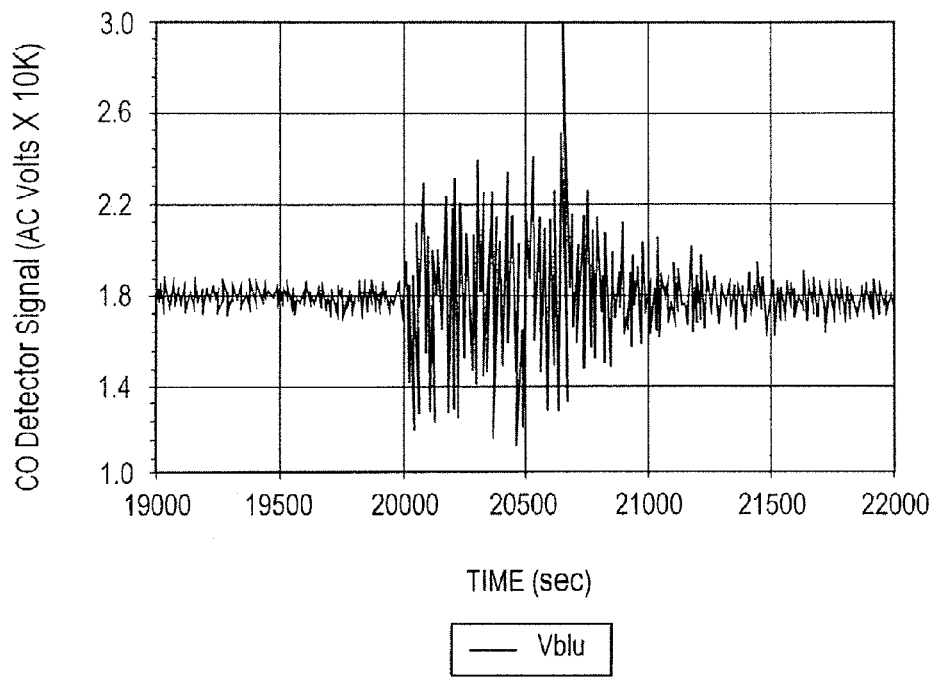
FIG. 1C illustrates high frequency noise variations as the sensor responds to increasing concentrations of a selected gas.
Figure 2:
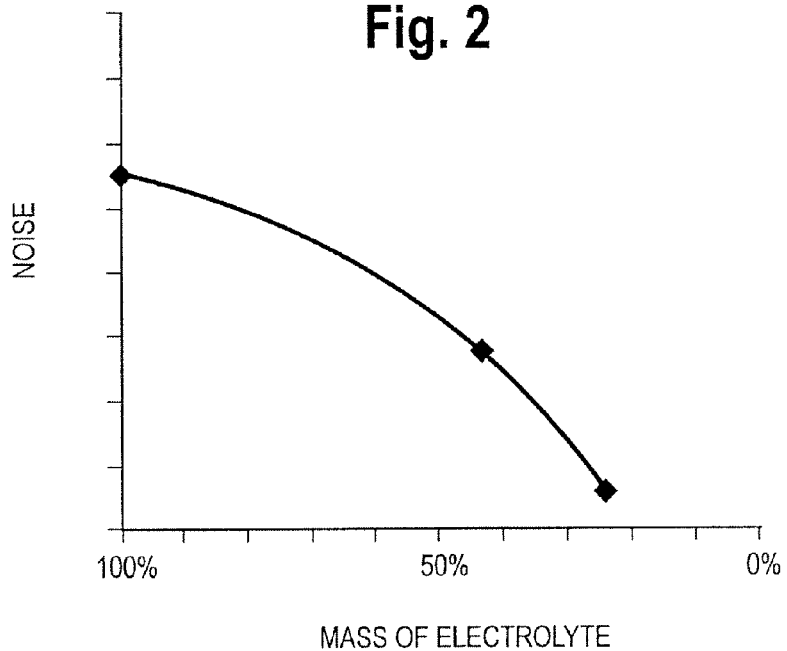
FIG. 2 is a graph illustrating noise as a function of mass of electrolyte of a sensor.

The electrical signals from an electrochemical sensor exhibit noise that is related to the level of sensed gas, see FIGS. 1A-1C. If the sensor electrolyte dries out, there is less electrical activity to generate noise and the noise level will fall. FIG. 2 illustrates an exemplary relationship between the mass of electrolyte and the noise level with no gas present. However, before the characteristics in this graph are exhibited, the noise level may actually rise during the final stages of drying before decreasing. Algorithms in the processor can use the increase in noise above a normal expected value to anticipate a pending fault condition.

Figure 3:
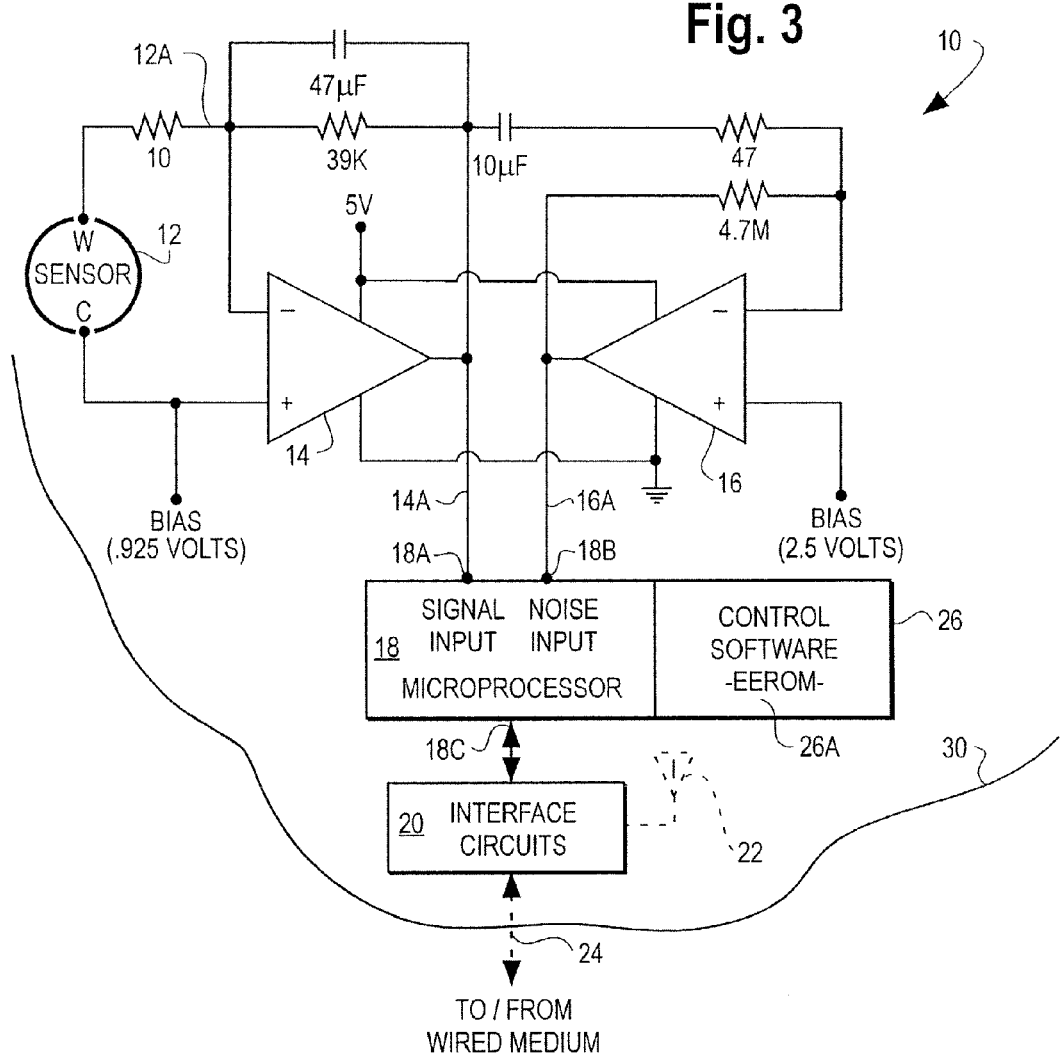
FIG. 3 is a block diagram of an exemplary detector in accordance with the invention.

Relative to FIG. 3, a gas detector 10 which embodies the present invention includes an electrochemical sensor 12 which has an output, line 12a, that is coupled to a pair of operational amplifiers 14, 16. The amplifier 14 provides a buffered output of the signal from sensor 12 and is configured as a relatively low pass filter and current-to-voltage converter, see FIG. 1, which is associated with the output signal from the sensor 12. An output 14a from operational amplifier 14 can be coupled to a sensor signal input port 18a of a programmable processor 18.

Operational amplifier 16 is configured as a high pass filter with additional gain and responds only to the high frequency noise in the signal from the operational amplifier 14, line 14a. The combination of the low pass characteristics of amplifier 14 and the high pass characteristics of amplifier 16 create a band pass for the noise. That signal is coupled, via line 16a, to a noise input port 18b of the processor 18. Processor 18 thus has access to a concentration signal, line 14a, and an associated noise signal, line 16a.

Processor 18 can in turn be coupled via output port 18c to interface circuits 20 as would be understood by those of skill in the art. Circuitry 20 can include an rf antenna, indicated in phantom, 22 for wireless configurations. Alternately, interface circuits 20 can couple signals to and from a wired medium 24. Detector 10 can thus communicate with an external alarm system, for example, as disclosed in Tice et al. U.S. Pat. No. 6,320,501 entitled "Multiple Sensor System for Alarm Determination with Device-to-Device Communications", assigned to the assignee hereof and incorporated herein by reference. It will be understood that neither of the detailed configurations of the interface circuits 20 nor the type of medium, wired or wireless, are limitations of the present invention.

Processor 18 operates in accordance with prestored control software 26 which could be stored, for example, in electrically eraseable read only memory EEPROM 26a. The detector 10 can be contained within and carried by a housing 30 as would be understood by those of skill in the art.

The processor 18 in combination with control software 26 can carry out signal processing in response to signal inputs, port 18a and noise inputs, port 18b. Exemplary processing is discussed subsequently relative to FIGS. 4, 5.

Figure 4:
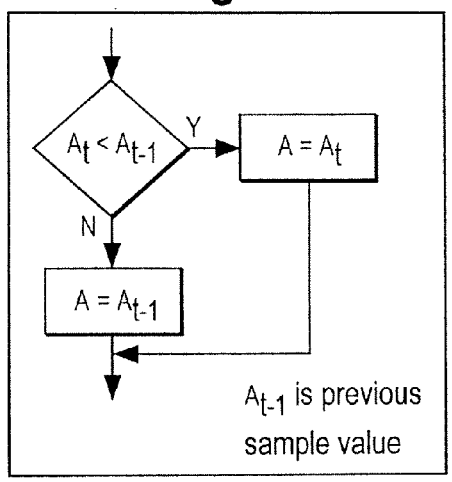
FIG. 4 is a flow diagram of one aspect of the present invention.

In order to make a meaningful measurement of the noise level, it is important to remove transients from the signal. The transients can be removed signal processing carried out by processor 18. One exemplary form of such processing selects the smaller of two time sequential signal values and uses the smaller value in place as the signal value. FIG. 4 illustrates this processing. Other methods can be used such as averaging or selecting the smaller of more than two time sequential signals.

The processor 18 can now establish the noise level in the signal of line 14a. Different methods can be used. The preferred method is to determine an average of the maximums of the signal (AvgMAX) and an average of the minimums (AvgMIN) of the signal over an extended period of time. The noise level (NL) can then be established: NL=AvgMAX−AvgMIN.

The extended period of time would be selected as would be understood by those of skill in the art such to follow drifting in the sensor signal without significantly changing NL measurements. If a gas is sensed, the signals will increase rapidly. However, this can cause an error in the calculation of NL. The calculation of the NL is the temporarily disabled until the signal again stabilizes within expected levels. The NL is then used subsequently to determine the sensitivity of the sensor.

The sensor will normally drift over time as the conditions change. The drift range (DR) is calculated over a long period of time to detect when the detector is deviating from normal. Normal expected range of drifting can be stored in memory, such as EEPROM 26a and the drift range compared to the expected range. Variations from the expected range can be used in the determination of the sensitivity.

Another indication of the sensor condition can be established by measuring the capacitance of the electrochemical sensor 12. This can be accomplished by coupling an electrical current to the sensor 12 and measuring the response signal over time. A capacitance value (C) can then be calculated and applied later in determining the sensitivity. It should be noted that C by itself is not a direct indicator of sensitivity of the electrochemical sensor. It is an indirect indicator that is factored into the functions for sensitivity calculation and sensor life-time.

The determinations of NL, DR, and C can be affected by environmental conditions such as temperature. Therefore, these values can be compensated according to predetermined relationships as would be understood by those of skill in the art. The measurement of humidity and time can also be used to predict drying of the electrolyte and thus factored into the function.

The sensitivity of the electrochemical sensor 12 can be determined as a function of NL, DR, C, and TIME. The addition of the manufacturer provided sensitivity (FS) information can be used to calculate an sensitivity adjustment factor (SA) such that SA=f{NL, DR, C, TIME, FS}. As the detector degrades in performance, the SA value will increase as a non-linear function.

The SA can be applied to compensate the sensor signals (CSS) back towards the original factory calibration. One of the TIME relationships can include a normal expected degrading of the electrochemical sensor over time due to the eroding of the electrode surfaces. This may be in the range of 5% change per year and would normally be established by a manufacturer of sensor 12. Another TIME relationship can be the averaging time of the routines such that transient conditions are further reduced and these TIME relationships can range from short term for NL to long term for DR.

As the SA value increases, it is also be an indication that the remaining sensor life time (SLT) is decreasing. If SLT decreases such that it is below a dynamic threshold based upon NL, DR, C, and TIME, then a trouble indication can be generated so the sensor can be replaced. In the meantime, the processor 18 and control program 26 will continue to attempt to maintain the original factory calibration.

As noted above, the signal, line 14a, will increase with the specified gas being present. An alarm can be established based upon predetermine routines as a function of CSS, gas alarm threshold(s), and TIME as illustrated in FIG. 5.

In accordance with the above, FIG. 5 illustrates steps of an exemplary method 100. In a step 102 the output from sensor 12 is obtained via processor 18. In a step 104 the transient signals, as discussed above, are removed therefrom.

In a step 106 a running average of maximum noise signals is established. In a step 108, a running average of minimum noise values is established.

The noise level NL is calculated in step 110 as discussed above. In step 112 the average CO signal is established.

A maximum average CO signal over a predetermined time interval is established in step 114. In step 116 the minimum of the average CO signal value over the time period is established.

A drift value is established in step 118. The capacitance of the sensor 12 can be established by any one of a variety of known methods, step 120.

The sensitivity adjustment for the signal could be established as a function of noise level, drift and capacitance in step 122. In step 124 the sensitivity adjustment is established. Compensated sensor signals can be established in step 126.

In step 128 a determination can be made of remaining sensor lifetime as a function of maximum lifetime under ideal conditions and the previously determined sensitivity adjustment, step 124. If the sensor lifetime is less than a predetermined value, step 130, then a trouble indicator can be communicated from processor 18 via interface circuits 20 to an alarm system wherein detector 10 is installed. Finally, in a step 132, the processor 18 can output an alarm indication if a function which is based on compensated sensor signals and time crosses a gas alarm threshold.

This method can also supervise the connection of circuitry to the electrochemical sensor. If the sensor is removed from the circuitry, the NL will immediately fall to the level of the circuitry noise. The new measured NL level can cause a re-calculation of the SA that then is applied to the SLT prediction that would likely end up below a function value resulting from N, DR, C, and TIME. This will result in a trouble indication so that the sensor can be serviced to restore operation.

One of the dynamic aspects of the present invention is that multiple factors can be used to determine the sensitivity adjustment over time. These values of NL, DR, and C can combine differently over time according to a predetermined function to adjust the sensitivity and also determine the SLT so sensor maintenance can be performed when required. A significant change in the value of NL, DR, or C can cause an immediate re-calculation of the SA and SLT. A period of time can also trigger this re-calculation.

Because the equations are dynamic, no internal predetermined SLT threshold is used. Rather, new SLT thresholds are calculated on demand after sensor values are received by the processing routines. The result is a more robust detector that adjusts itself to the present condition of the sensor.

The generation of alarm and trouble separately enables the system to which the detector, such as detector 10, is coupled to exhibit a proper response to the detector's condition. The output indications can be transmitted in communication messages, different wireless patterns, or different audio patterns which are emitted from the detector 10.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A method comprising:
   sensing an electrical signal of an electrochemical gas sensor indicative of a selected condition;
   sensing noise in the electrical signal;
   comparing the noise, to pre-stored indicia, and responsive thereto adjusting a sensitivity parameter associated with the selected condition.

2. A method as in claim 1 where the sensitivity parameter is adjusted inversely relative to the results of the comparing.

3. A method as in claim 1 where the sensing comprises sensing stochastic noise.

4. A method as in claim 1 which includes estimating, responsive to sensed noise, a lifetime parameter of a source of the signal.

5. A method as in claim 1 which includes sensing an initial noise parameter and storing same as the pre-stored indicia.

6. A method as in claim 5 which includes using the sensitivity parameter to make a lifetime estimate.

7. A method as in claim 6 which includes transmitting an indicia indicative of remaining lifetime to a remote location to facilitate maintenance.

8. A method as in claim 1 where sensing noise includes sensing stochastic noise in the electrical signal.

9. A method as in claim 1 where in adjusting a sensitivity parameter includes adjusting a gain parameter.

10. A method as in claim 1 which includes estimating a predetermined remaining lifetime parameter.

11. A method as in claim 10 where responsive to the estimated remaining lifetime parameter, a replacement indicator is generated.

12. A method as in claim 10 where estimating includes providing software carried on a computer readable medium for estimating the remaining lifetime parameter.

13. A method as in claim 12 which includes generating a replacement indicator.

14. A method as in claim 1 where sensing noise includes providing software carried on a computer readable medium for evaluating a stochastic noise level in the electrical signal.

15. A method of adjusting the sensitivity in an electrochemical gas sensor that produces an output signal comprising:
    establishing a first sensitivity value for an electrochemical gas sensor;
    measuring the electrical noise level in the output signal of the gas sensor;
    establishing a reference electrical noise value representative of the gas sensor operating at the first sensitivity value; and
    adjusting a sensitivity value from a first sensitivity value to a different sensitivity value based, at least in part, on the measured electrical noise level and the reference electrical noise level.

16. A method as in claim 15 where the adjusted sensitivity value is used to establish a time-value representative of the time remaining until the electrochemical sensor should be replaced.

17. A method as in claim 16 where the time-value is compared to a predetermined replacement threshold value and a fault indication given if the time-value is less than the said replacement threshold value.

18. A method as in claim 17 where the fault indication is different than an alarm indication.

19. A method as in claim 16 which includes establishing a remaining sensor lifetime and comparing it to a predetermined replacement threshold value to determine if the sensor should be replaced.

20. A method as in claim 15 where the adjusting includes the averaging of electrical noise in the signals from the sensor over time to determine the measured electrical noise level.

21. A method as in claim 15 where the adjusting excludes the measured electrical noise level when gas is present for the sensor to respond to.

22. A method as in claim 15 where the adjusting includes, at least in part, the measured electrical noise level during the sensing of gas by the sensor.

23. A method of adjusting the sensitivity in an electrochemical gas sensor which produces an output signal comprising:
    establishing a sensitivity value for the electrochemical sensor to relate its output signal to a gas concentration, the sensitivity value having a first sensitivity value representative of a non-degraded sensor,
    measuring an electrical noise level in the output signal of the electrochemical gas sensor during the sensing of gas;
    establishing a reference electrical noise level representative of the electrochemical gas sensor operating at the first sensitivity value; and
    adjusting the sensitivity value from the first sensitivity value to a different sensitivity value based, at least in part, upon the electrical noise level in the output signal of the electrochemical gas sensor during the sensing of gas.

24. A method of adjusting the sensitivity in an electrochemical gas detecting apparatus, comprising the steps of:
- establishing a sensitivity value for the electrochemical sensor to relate an electrical output signal to a concentration of a selected gas, the sensitivity value having a first sensitivity value representative of a non-degraded sensor;
- measuring a noise level in the output signal of the electrochemical gas sensor in the absence of the selected gas;
- measuring the electrical noise level in the output signal of the electrochemical gas sensor during the sensing of gas;
- establishing a reference electrical noise level representative of the electrochemical gas sensor operating at the first sensitivity value; and
- adjusting the sensitivity value from the said first sensitivity value to a different sensitivity value based at least in part upon the said electrical noise level in the output signal of the electrochemical gas in response to sensing the selected gas and in the absence of the selected gas.

* * * * *